US009745259B2

(12) United States Patent
Wang et al.

(10) Patent No.: US 9,745,259 B2
(45) Date of Patent: Aug. 29, 2017

(54) PROCESS FOR PREPARING ALCOHOL ETHER SULFATES

(71) Applicant: Chevron Oronite Company LLC, San Ramon, CA (US)

(72) Inventors: Ping Wang, Fremont, CA (US); Curtis Bay Campbell, Hercules, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 14/958,972

(22) Filed: Dec. 4, 2015

(65) Prior Publication Data

US 2017/0158625 A1    Jun. 8, 2017

(51) Int. Cl.
*C07C 303/24*    (2006.01)
(52) U.S. Cl.
CPC .................. *C07C 303/24* (2013.01)
(58) Field of Classification Search
CPC .................................... C07C 303/24
See application file for complete search history.

(56) References Cited

U.S. PATENT DOCUMENTS 6,046,152 A * 4/2000 Vinson .................. A61K 8/463
510/119
2015/0307428 A1* 10/2015 Buechele .............. C07C 303/24
558/21

OTHER PUBLICATIONS

L.D. Talley "Hydrolytic Stability of Alkylethoxy Sulfates" SPE Reservoir Engineering, Feb. 1988, 235-242.
M. Minana-Perez, A. Graciaa, J. Lachaise and J.-L. Salager "Solubilization of polar oils with extended surfactants" Colloid Surface A 1995, 100, 217-224.
D.W. Roberts "Sulfation Technology for Anionic Surfactant Manufacture" Org. Process Res. Dev. 1998, 2, 194-202.
Y. Wu, P. Shuler, M. Blanco, Y. Tang and W.A. Goddard "A Study of Branched Alcohol Propoxylate Sulfate Surfactants for Improved Oil Recovery" SPE 95404, SPE Annual Technical Conference and Exhibition, Dallas, TX, Oct. 9-12, 2005.
S. Adkins, P.J. Liyanage, G.W. Pinnawala Arachchilage, T. Mudiyanselage, U. Weerasooriya and G.A. Pope "A New Process for Manufacturing and Stabilizing High-Performance EOR Surfactants at Low Cost for High-Temperature, High-Salinity Oil Reservoirs" SPE 129923, SPE Improved Oil Recovery Symposium, Tulsa, OK Apr. 24-28, 2010.

* cited by examiner

*Primary Examiner* — Rosalynd Keys
(74) *Attorney, Agent, or Firm* — Thomas P. Weber

(57) ABSTRACT

A process for preparing an alcohol ether sulfate is disclosed which comprises: (a) sulfating an alkoxylated alcohol; and (b) neutralizing the sulfated product of step (a) in the presence of a base and a co-solvent having a flash point of at least 60° C.

13 Claims, 2 Drawing Sheets

PROCESS FOR PREPARING ALCOHOL ETHER SULFATES

TECHNICAL FIELD

This disclosure relates generally to a process for preparing stabilized alcohol ether sulfates suitable for use in enhanced oil recovery.

BACKGROUND

Crude oil production from oil in subterranean reservoirs may involve use of various flooding methods as the natural forces that are used in the "primary recovery" process become depleted. A large portion of the crude oil may have to be driven out of the formation in "secondary" or "tertiary" recovery processes. In addition, some reservoirs may not have sufficient natural forces for oil production even by primary recovery processes. The production of crude oil using such flooding methods is one example of an enhanced oil recovery process.

One trend in the petroleum industry now is to plan exploitation of the oil field at the beginning of the project. Injecting a displacing fluid or gas may begin early, long before the complete depletion of the field by primary recovery processes. Methods for improving displacement efficiency or sweep efficiency may be used at the very beginning of the first injection of a displacing fluid or gas, rather than under secondary and tertiary recovery conditions.

The least expensive and easiest method of flooding a subterranean reservoir for the production of crude oil is by injecting a liquid or a gas into the well to force the oil to the surface. Water flooding is the most widely used fluid. However, water does not readily displace oil because of the immiscibility of water and oil and/or the high interfacial tension between the two liquids.

The addition of chemicals to modify the properties of the flooding liquid is well known in the art. Surfactants are one class of chemical compounds that have been used in aqueous media for enhanced oil recovery. Surfactants have been found to effectively lower the interfacial tension between oil and water and enabling the oil droplets to flow more easily through the channels of the reservoir.

Alcohol ether sulfates are a class of anionic surfactants used in enhanced oil recovery. Alcohol ether sulfates are made by reacting alkoxylated alcohols with a sulfating agent to convert the alcohol functionality into a sulfuric acid semi-ester (—C—O—SO$_3$H group). The sulfuric acid semi-esters are normally neutralized quickly after formation because they are generally not stable (see D. W. Roberts, Org. Process Res. Dev. 1998, 2, 194-202). As a result, alcohol ether sulfates tend to be difficult to manufacture.

It has now been found that preparation and neutralization of the sulfuric acid semi-esters is possible and in the presence of a co-solvent results in an alcohol ether sulfate product having improved neutralization and storage stability.

SUMMARY

In one aspect, there is provided a process for preparing an alcohol ether sulfate, the process comprising: (a) sulfating an alkoxylated alcohol; (b) neutralizing the sulfated product of step (a) in the presence of a base and a co-solvent having a flash point of at least 60° C.

DETAILED DESCRIPTION

Introduction

Figure 1:
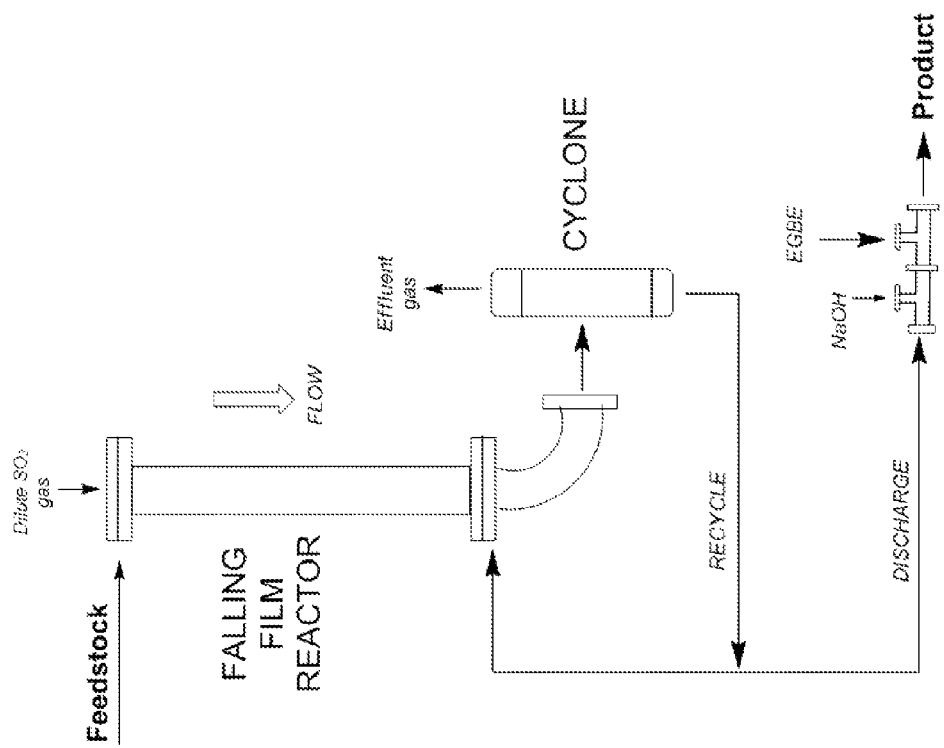
FIG. 1 depicts a pilot plant sulfation process flow diagram as employed in Example 1.

The following terms and abbreviations will be used throughout the specification and will have the following meanings unless otherwise indicated.

The term "alcohol ether sulfate" refers to compound having the following general structure:

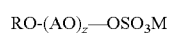

$$RO\text{-}(AO)_z\text{-}OSO_3M$$

where R is a $C_{12}$-$C_{36}$ aliphatic hydrocarbon group; AO represents one or more $C_2$-$C_4$ alkylene oxide units (e.g., ethylene oxide, propylene oxide); z≥1; and M is an alkali metal cation, an alkaline earth metal cation, an ammonium cation or a substituted ammonium cation. The alkylene oxide units may be incorporated randomly or in blocks.

The terms "sulfuric acid semi-ester" and "acid ester" refer to a compound having a C—O—SO$_3$H group.

The term "co-solvent" as used herein refers to alcohols, ethers and/or a range of nonionic materials.

The term "aliphatic" denotes a hydrocarbon moiety that may be straight-chain (i.e., unbranched), branched, or cyclic and may be completely saturated or may contain one or more units of unsaturation, but which is not aromatic. Suitable aliphatic groups include, but are not limited to, linear or branched, alkyl and alkenyl groups.

The term "flash point" refers to the lowest temperature at which a volatile liquid can vaporize to form an ignitable mixture in air. The flash point can be measured, e.g., by the ASTM D3828 or ASTM D93 closed-cup methods and is an indication of the flammability of the liquid.

The "number average molecular weight" is abbreviated as $M_n$ and refers to the ordinary arithmetic mean of the molecular weight of individual molecules in a sample. It is defined as the total weight of all molecules in a sample divided by the total number of molecules in the sample. Experimentally, the number-average molecular weight ($M_n$) is determined by analyzing a sample divided into molecular weight fractions of species i having $n_i$ molecules of molecular weight $M_i$ through the formula $M_n = \Sigma M_i n_i / \Sigma n_i$. The number-average molecular weight can be measured by a variety of well-known methods including gel permeation chromatography, spectroscopic end group analysis, and osmometry. If unspecified, molecular weights of polymers given herein are number average molecular weights.

"Propylene glycol" (also 1,2-propanediol) is abbreviated as PG.

"Ethylene glycol n-butyl ether" (also 2-butoxyethanol) is abbreviated as EGBE.

"Propylene oxide" (also —$C_3H_6O$—) is abbreviated as PO.

"Ethylene oxide" (also —$CH_2CH_2O$—) is abbreviated as EO.

Alkoxylated Alcohol

Alkoxylated alcohols can be prepared in a manner in principle known to those of skill in the art. Normally, at least one aliphatic alcohol is reacted with alkylene oxide (e.g., ethylene oxide, propylene oxide) in the presence an alkoxylation catalyst. Alkoxylations are usually catalyzed by a base (e.g., KOH), but other catalysts such as double metal cyanide complexes can also be used (see, e.g., U.S. Pat. No. 5,482,908).

In one embodiment, the alkoxylated alcohol useful in the process described herein can be represented by the following structure (1):

$$RO-(AO)_z-OH \qquad (1)$$

where R is a $C_{12}$-$C_{40}$ (e.g., a $C_{18}$-$C_{36}$ or a $C_{24}$-$C_{32}$) aliphatic hydrocarbon group; AO represents one or more $C_2$-$C_4$ alkylene oxide units (e.g., ethylene oxide, propylene oxide) and $z \geq 1$ (e.g., $100 \leq z \geq 1$). The alkylene oxide units may be incorporated randomly or in blocks.

The aliphatic hydrocarbon group (R) originates from an aliphatic alcohol (R—OH) and may represent a mixture of chain lengths, may be saturated or unsaturated, may be linear or branched, or any combination of the foregoing. Preferably, the aliphatic hydrocarbon group (R) is an alkyl group, more preferably a branched alkyl group.

The aliphatic alcohol (R—OH) from which the aliphatic hydrocarbon group (R) originates may be a primary or a secondary alcohol, preferably a primary alcohol. In one embodiment, the aliphatic alcohol is a $C_{12}$-$C_{40}$ (e.g., a $C_{18}$-$C_{36}$, a $C_{24}$-$C_{32}$) Guerbet alcohol. As used herein, a "Guerbet alcohol" refers to a mono-functional, primary alcohol comprising at least one branching at the carbon atom adjacent to the carbon atom carrying the hydroxyl group. Chemically, Guerbet alcohols are described as 2-alkyl-1-alkanols.

In one embodiment, the alkoxylated alcohol useful in the process described herein is a block co-polymer represented by the following structure (2):

$$RO-(C_3H_6O)_x-(C_2H_4O)_y-OH \qquad (2)$$

wherein R is a $C_{12}$-$C_{40}$ (e.g., a $C_{18}$-$C_{36}$ or a $C_{24}$-$C_{32}$) aliphatic hydrocarbon group; $x > 1$; $y > 1$; and $x+y \leq 100$. As used herein, a "block co-polymer" refers to a polymer composed of two or more different polymers arranged in segments or "blocks" of each constituent polymer.

In one embodiment, x may be in a range from 5 to 50 (e.g., from 5 to 45, from 10 to 45, from 5 to 40, from 10 to 50, from 10 to 45, from 10 to 40, from 15 to 50, from 15 to 45, from 15 to 40, from 20 to 50, from 20 to 45, from 20 to 40, from 25 to 50, from 25 to 45, or from 25 to 40).

In one embodiment, y may be in a range from 5 to 50 (e.g., from 5 to 45, from 5 to 40, from 5 to 35, from 5 to 30, from 5 to 25, from 5 to 20, from 5 to 15, from 10 to 50, from 10 to 45, 10 to 40, from 10 to 35, from 15 to 50, from 15 to 45, from 15 to 40, from 15 to 35, from 20 to 50, from 20 to 45, from 20 to 40, from 20 to 35, from 25 to 50, from 25 to 45, from 25 to 40, or from 25 to 35).

In one embodiment, x may be in a range from 20 to 50 and y may be in a range from 5 to 15. In one embodiment, x may be in a range from 20 to 50 and y may be in a range from 20 to 50.

In one embodiment, the alkoxylated alcohol generally comprises more propylene oxide units (x) than ethylene oxide units (y), wherein the ratio of ethylene oxide units to propylene oxide units (y/x) is in the range from 0.01 to 1 (e.g., from 0.1 to 1, from 0.1 to 0.5, from 0.25 to 1, or from 0.5 to 1).

Sulfation

Sulfation of the alkoxylated alcohol may be performed by any method known to those of skill in the art. The sulfation is typically carried out in a continuous falling film tubular reactor maintained at a temperature from 30° C. to 75° C. using sulfur trioxide ($SO_3$) as the sulfating agent. The mole ratio of $SO_3$ to alkoxylated alcohol is typically maintained at a range of from 0.8 to 1.2:1.

Other sulfating agents, such as chlorosulfonic acid or sulfamic acid, may also be employed. Preferably, the alkoxylated alcohol is sulfated with sulfur trioxide diluted with air (e.g., 3-5% $SO_3$ mole fraction in process air).

Sulfate Neutralization

The resulting sulfated products are sulfuric acid semi-esters ("acid esters") which are generally not stable and must therefore immediately be transferred into a neutralization cycle in which it is converted, since otherwise elimination of sulfur trioxide will occur. Elimination of $SO_3$ may lead to alkoxylate chain degradation with concomitant formation of undesirable by-products such as 1,4-dioxane and/or dimethyl 1,4-dioxane.

Neutralization of the acid ester may be carried out in a continuous or batch process by any method known to one skilled in the art.

Generally, the neutralization step is carried out in an in-line mixing reactor in which the acid ester, an organic or inorganic base, and a water-miscible co-solvent are mixed and the temperature is maintained between 20° C. and 80° C. As used herein, a "water-miscible co-solvent" refers to an organic co-solvent that can form a monophasic solution with water at the temperature at which the reaction is carried out.

The acid ester may be neutralized using an aqueous alkali metal hydroxide (e.g., sodium hydroxide or potassium hydroxide), an aqueous alkaline earth metal hydroxide (e.g., magnesium hydroxide or calcium hydroxide), or bases such as ammonium hydroxide, substituted ammonium hydroxide, sodium carbonate or potassium hydrogen carbonate. Preferably, the acid ester is neutralized using an aqueous alkali metal hydroxide.

A co-solvent is employed to aid dissolution of the acid ester in water. The co-solvent can be any water-miscible fluid having a flash point of at least 60° C.

Suitable co-solvents may include polyhydric alcohols, alkylene glycol monoethers, polyalkylene glycols, polyalkylene glycol monoethers.

Examples of suitable polyhydric alcohols include $C_2$-$C_6$ alkylene glycols, particularly $C_2$-$C_4$ alkylene glycols such as ethylene glycol, propylene glycol, and butylene glycol.

Examples of suitable alkylene glycol monoethers include alkylene glycol mono($C_1$-$C_6$ alkyl)ethers, particularly alkylene glycol mono($C_1$-$C_4$ alkyl)ethers such as ethylene glycol n-butyl ether and propylene glycol n-butyl ether.

Examples of suitable polyalkylene glycols include poly($C_2$-$C_4$ alkylene)glycols having 2-10 $C_2$-$C_4$ alkylene glycol units such as diethylene glycol, triethylene glycol, tetraethylene glycol, polyethylene glycol 300, polyethylene glycol 400, dipropylene glycol, tripropylene glycol, and the like.

Examples of suitable polyalkylene glycol monoethers include poly($C_2$-$C_4$ alkylene)glycol mono($C_1$-$C_6$ alkyl) ethers having 2-50 alkylene glycol units per molecule such as diethylene glycol methyl ether, diethylene glycol ethyl ether, diethylene glycol n-butyl ether, triethylene glycol methyl ether, triethylene glycol ethyl ether, triethylene glycol n-butyl ether, dipropylene glycol methyl ether, tripropylene glycol methyl ether, and polyethoxylated $C_2$-$C_4$ alcohols having from 5 to 25 ethylene oxide units per molecule.

Preferably, the co-solvent is selected from the group consisting of ethylene glycol, propylene glycol, ethylene glycol n-butyl ether, diethylene glycol, triethylene glycol, tetraethylene glycol, dipropylene glycol, tripropylene glycol, diethylene glycol methyl ether, diethylene glycol ethyl ether, diethylene glycol n-butyl ether, triethylene glycol methyl ether, triethylene glycol ethyl ether, triethylene glycol n-butyl ether, polyethoxylated $C_2$-$C_4$ alcohols having from 5 to 25 ethylene oxide units per molecule, and combinations thereof.

The co-solvent may have a flash point of at least 65° C., at least 70° C., or at least 75° C. The co-solvent may have a flash point of 400° C. or less, 350° C. or less, 300° C. or less, 250° C. or less, or even 200° C. or less. For example, the co-solvent may have a flash point of from 60° C. to 400° C. (e.g., from 60° C. to 350° C., from 60° C. to 300° C., from 60° C. to 250° C., from 60° C. to 225° C., from 60° C. to 200° C., from 65° C. to 400° C., from 65° C. to 350° C., from 65° C. to 300° C., from 65° C. to 250° C., from 65° C. to 225° C., from 65° C. to 200° C., from 70° C. to 400° C., from 70° C. to 350° C., from 70° C. to 300° C., from 70° C. to 250° C., from 70° C. to 225° C., from 70° C. to 200° C., from 75° C. to 400° C., from 75° C. to 350° C., from 75° C. to 300° C., from 75° C. to 250° C., from 75° C. to 225° C., or from 75° C. to 200° C.).

In the neutralization step, the weight ratio of the co-solvent to the acid ester is suitably from 0.01:1 to 10:1, (e.g., from 0.1:1 to 5:1, from 0.25:1 to 3:1, or from 0.5:1 to 1.5:1).

Preferably, the process described herein is a continuous process. By "continuous", it is meant a system that operates without interruption or cessation. For example, a continuous process to produce an alcohol ether sulfate would be one where the reactants are continually introduced into one or more reactors and alcohol ether sulfate product is continually withdrawn.

In one embodiment, the resulting product is an alcohol ether sulfate represented by the following structure (3):

$$RO\text{—}(C_3H_6O)_x\text{—}(C_2H_4O)_y\text{—}OSO_3M \quad (3)$$

wherein R, x, and y are as described herein above and M is an alkali metal cation, an alkaline earth metal cation, an ammonium cation or a substituted ammonium cation.

In one embodiment, the resulting alcohol ether sulfate has a number average molecular weight ($M_n$) of at least 2000 (e.g., at least 2500, at least 3000, at least 3500, from 2000 to 6000, from 2000 to 5500, from 2000 to 5000 g/mol, from 2000 to 4500, from 2000 to 4000, from 2500 to 6000, from 2500 to 5500, from 2500 to 5000, from 2500 to 4500, or from 2500 to 4000).

EXAMPLES

The following illustrative examples are intended to be non-limiting.

Example 1

Pilot Plant Sulfation of High Molecular Weight Alcohol Polyether Alcohol Feedstock Pilot plant sulfation of the feedstock was accomplished using a tubular thin film reactor as illustrated in FIG. 1. The feedstock was a 2900 MW block propoxylate/ethoxylate co-polymer alcohol (ISOFOL® 28-$(PO)_{35}(EO)_{10}$—H). ISOFOL® 28 (Sasol Performance Chemicals) is 2-dodecyl-hexadecanol. Dilute $SO_3$ gas is contacted with the organic feedstock. The reactor consists of a nominal 0.6 inch inside diameter water-jacketed stainless steel tube, 5 feet long, mounted vertically. The feedstock is metered through a mass flow meter and temperature controlled jacketed tubing before entering the film reactor. The feedstock enters a weir at the top of the reactor and is distributed uniformly around the circumference of the reactor tube. The dilute $SO_3$ gas stream enters from above the reactor tube. As the gas and liquid moved down the reactor, the $SO_3$ is absorbed by the feedstock and reacts with the feedstock. Exiting the reactor, the gas and liquid enter a cyclone where the two phases are separated. The liquid exiting from the bottom of the cyclone is pumped through a cooling heat exchanger. A portion of the cooled liquid is returned just below the bottom of the reactor tube where it is mixed with the hotter gas and liquid exiting the reactor. The recycle of liquid serves to both quench cool the fresh reaction products and scavenge unabsorbed $SO_3$. The vent gas exiting the top of the cyclone is directed to $SO_2$ absorber and then a mist pad. The portion of the cooled liquid that is not recycled back to the reactor is transferred to the neutralizer. The crude acid was then quenched with 50 wt. % aqueous NaOH and then diluted approximately 30% by weight with ethylene glycol n-butyl ether to afford the final product.

The 2900 molecular weight block propoxylate/ethoxylate co-polymer alcohol samples were sulfated using $SO_3$/Air and the following general conditions:

$SO_3$ Loading=about 0.1 kg/hr-cm
$SO_3$ in Air Concentration=0.8 vol. %
Air/$SO_3$ Temperature=40° C.
Feed Temperature=70-75° C.
Neutralizer Temperature=50° C.

Product was made using the following six different process conditions described in Table 1:

TABLE 1

| Condition | $SO_3$/Feedstock Mole Ratio | Feedstock Temp. to Reactor (° C.) | Reactor Temp. (° C.) |
|---|---|---|---|
| 1 | 1.20 | 70 | 60 |
| 2 | 1.10 | 70 | 60 |
| 3 | 1.00 | 70 | 60 |
| 4 | 0.90 | 70 | 60 |
| 5 | 1.20 | 75 | 75 |
| 6 | 1.00 | 75 | 75 |

Table 2 summarizes the analytical properties of the product obtained by the sulfation of the 2900 MW alcohol polyether alcohol feedstock.

TABLE 2

| Properties of Neutralized Product Produced Using a Pilot Plant Sulfation Process | | | | | | |
|---|---|---|---|---|---|---|
| Condition | % Actives[1] | % Actives 3 Months After Production | 1,4-Dioxane Content[2] (ppm) | Dimethyl-1,4-dioxane Content (ppm) | pH at Time of Production[3] | pH 3 Months After Production |
| 1 | 60, 61 | 56 | 6.7 | 14.7 | 11.2 | 11.0 |
| 2 | 56, 54 | 61 | 5.7 | 15.0 | 10.8 | 11.0 |
| 3 | 53, 51 | 57 | 5.8 | 12.8 | 11.0 | 11.0 |
| 4 | 50, 50 | 57 | 5.6 | 8.9 | 10.9 | 11.0 |

TABLE 2-continued

Properties of Neutralized Product Produced Using a Pilot Plant Sulfation Process

| Condition | % Actives[1] | % Actives 3 Months After Production | 1,4-Dioxane Content[2] (ppm) | Dimethyl-1,4-dioxane Content (ppm) | pH at Time of Production[3] | pH 3 Months After Production |
|---|---|---|---|---|---|---|
| 5 | 63, 62 | 58 | 6.0 | 9.0 | 11.0 | 11.0 |
| 6 | 52, 52 | 55 | 5.7 | 6.9 | 11.1 | 11.0 |

[1]Determined via HYAMINE ® titration using 3200 for the sodium salt molecular weight
[2]Measured by gel permeation liquid chromatography
[3]pH measurements were made on a 10 wt. % aqueous solution of the neutralized product using a calibrated pH electrode Example 2

Figure 2:
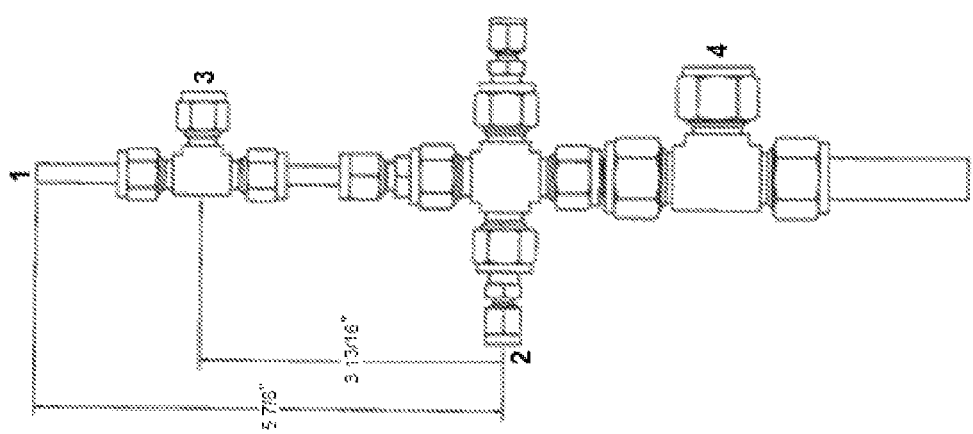
FIG. 2 depicts a laboratory sulfation reactor top assembly as employed in Example 2.

Laboratory Thin Film Sulfation of High Molecular Weight Alcohol Polyether Alcohol Laboratory sulfation of the same feedstock used in Example 1 (2900 MW block propoxylate/ethoxylate copolymer alcohol: ISOFOL® 28-$(PO)_{35}(EO)_{10}$—H) was accomplished in a metal, water jacketed, falling film tubular reactor (0.6 cm ID and 152 cm in length) with the reactor top assembly as shown in FIG. 2, where 1=$SO_3$/air inlet; 2=feedstock inlet; 3=makeup air inlet; and 4=cooling water inlet for the falling film reactor. The process parameters were used:

$SO_2$ Rate=2.0 L/hr
$SO_2$ to $SO_3$ Conversion=87%
Air with $SO_2$ Rate=150 L/h
Makeup Air Rate=30 L/min
Feed Temperature=65° C.
Falling Film Reactor Cooling Temperature=90° C.
Feedstock Feed Rate=3.45 g/min The sulfates produced using the above conditions were found to be fairly stable upon storage at room temperature. Table 3 shows the activity change of different batches of acid as a function of time when stored at room temperature.

TABLE 3

Sulfate Storage Stability at Room Temperature

| Time (Days) | Cyclohexylamine Titration Acid Activity (%) |
|---|---|
| 0 | 45.11 |
| 1 | 46.33 |
| 2 | 44.13 |
| 3 | 39.51 |
| 9 | 36.40 |
| 0 | 48.47 |
| 1 | 48.96 |
| 5 | 46.27 |
| 6 | 45.18 |
| 8 | 42.02 |
| 0 | 62.36 |
| 1 | 62.31 |
| 2 | 62.21 |
| 15 | 57.45 |
| 16 | 56.35 |
| 19 | 54.06 |
| 0 | 53.34 |
| 1 | 54.96 |
| 4 | 51.58 |
| 8 | 49.27 |

The acids produced were neutralized in batch as follows: to 30.0 grams of acid in a 250 mL PYREX® glass beaker was added varying aqueous amounts of NaOH (50 wt. % in water) followed by addition of a co-solvent followed by mixing at room temperature for 45 minutes. Two types of mixing were used: standard (Stnd) and high sheer (HS). Standard mixing consisted of an overhead mechanical stirrer (with a flat blade vertical turbine; 5 cm in diameter and 8 blades of 1 cm×1 cm dimension) at approximately 500 rpm. For high sheer mixing, a Silverson Model L4RT-A high shear mixer was used. The analytical data for the resulting neutralized products are summarized in Table 4.

TABLE 4

Properties of Neutralized Product Using Laboratory Thin Film Sulfation

| Entry | Acid Activity (%) | Caustic Added (g) | Co-Solvent (wt. % based on mass of acid) | Type of Mixing | pH[1] | % Actives of Neutralized Product[2] | Time (days) |
|---|---|---|---|---|---|---|---|
| A | 54.1 | 1.37 | $H_2O$ (50) | Stnd | 7.7 | 26.1 | 0 |
|   |      |      |             |      | 4.6 | 25.7 | 5 |
|   |      |      |             |      | 4.1 | 25.7 | 27 |
| B | 62.3 | 1.37 | $H_2O$ (130) | HS (2500 rpm) | 10.8 | 12.8 | 0 |
|   |      |      |             |      | 10.7 | 21.4 | 6 |
|   |      |      |             |      | 10.7 | 14.9 | 11 |
| C | 54.1 | 1.37 | $H_2O$ (50) | HS (500 rpm) | 3.7 | 23.7 | 0 |
|   |      |      |             |      | 3.7 | 23.3 | 5 |
|   |      |      |             |      | 3.7 | 25.1 | 27 |

TABLE 4-continued

Properties of Neutralized Product Using Laboratory Thin Film Sulfation

| Entry | Acid Activity (%) | Caustic Added (g) | Co-Solvent (wt. % based on mass of acid) | Type of Mixing | pH[1] | % Actives of Neutralized Product[2] | Time (days) |
|---|---|---|---|---|---|---|---|
| D | 62.2 | 1.37 | EGBE (50) | Stnd | 10.3 | 26.9 | 0 |
|   |      |      |           |      | 10.3 | 27.8 | 6 |
|   |      |      |           |      | 10.3 | 28.4 | 11 |
| E | 62.3 | 1.37 | EGBE (50) | HS (2500 rpm) | 10.4 | 11.8 | 0 |
|   |      |      |           |      | 10.4 | 20.5 | 6 |
|   |      |      |           |      | 10.7 | 19.3 | 11 |
| F | 54.1 |      | EGBE:H$_2$O 1:1 (50) | Stnd | 9 | 33.1 | 0 |
|   |      |      |           |      | 6.8 | 32.3 | 5 |
|   |      |      |           |      | 6.8 | 32.1 | 7 |
| G | 54.1 | 1.37 | EGBE (50) | HS (500 rpm) | 9.0 | 26.2 | 0 |
|   |      |      |           |      | 7.4 | 26.1 | 5 |
|   |      |      |           |      | 6.9 | 25.8 | 27 |
| H | 55 | 1.5 | PG:H$_2$O 1:1 (50) | Stnd | 10.6 | 29.5 | 2 |
|   |    |     |                     |      | 10.6 | 30.6 | 8 |
|   |    |     |                     |      | 10.6 | 34.8 | 20 |
| I | 55 | 1.5 | (CH$_3$)$_2$CHO—(EO)$_{10}$—OH:H$_2$O 1:1 (50) | Stnd | 11.1 | 31.6 | 2 |
|   |    |     |                     |      | 11.2 | 31.0 | 8 |
|   |    |     |                     |      | 10.9 | 32.3 | 20 |
| J | 49.3 | 1.5 | (CH$_3$)$_2$CHO—(EO)$_{20}$—OH:H$_2$O 1:1 (50) | Stnd | 10.9 | 31.5 | 2 |
|   |      |     |                     |      | 10.8 | 30.3 | 8 |
|   |      |     |                     |      | 11.0 | 31.5 | 20 |
| K | 49.3 | 1.5 | PG (50) | Stnd | 10.7 | 27.2 | 0 |
|   |      |     |         |      | 11.0 | 32   | 14 |
| L | 49.3 | 1.5 | (CH$_3$)$_2$CHO—(EO)$_{20}$—OH (50) | Stnd | 10.9 | 27.7 | 0 |
|   |      |     |         |      | 11.2 | 30.6 | 15 |

[1]pH measurements were made on a 1 wt. % aqueous solution of the neutralized product using a calibrated pH electrode
[2]Determined via HYAMINE ® titration using 2773 for the sodium salt molecular weight Entry A shows that using only water dilution of the acid and normal mechanical mixing with caustic results in incomplete neutralization. Entry B shows that using only water dilution of the acid and high sheer mixing at 2500 rpm with caustic results in neutralization, but the resulting product has low activity. Entry C shows that the using water only as the co-solvent and high sheer mixing at 500 rpm with caustic results in incomplete neutralization of the acid. Entry D shows that using only EGBE as the co-solvent during neutralization of the acid with caustic and standard mixing results in good neutralization and the pH of the product is stable. Entry E shows that using only EGBE as the co-solvent during neutralization of the acid with caustic and high shear mixing (2500 rpm) results in good neutralization but low activity. A comparison of Entries D and F shows that using a mixture of EGBE and water during neutralization of the acid with caustic and standard mixing is not as good as using only EGBE. Entries H-L show that neutralization of the acid with a variety of nonionic co-solvents, with or without water, and standard mixing provides better neutralization and product stability compared to water alone as the co-solvent.

Example 3

Laboratory Thin Film Sulfation of Extra High Molecular Weight Alcohol Polyether Alcohol Laboratory sulfation of an extra high molecular weight (3762 MW) block propoxylate/ethoxylate co-polymer alcohol feedstock (ISOFOL® 28-(PO)$_{35}$(EO)$_{30}$—H) was accomplished in a metal, water jacketed, falling film tubular reactor as described in Example 2 using the following process parameters:

SO$_2$ Rate=2.0 L/hr
SO$_2$ to SO$_3$ Conversion=87%
Air with SO$_2$ Rate=150 L/h
Makeup Air Rate=30 L/min
Feed Temperature=90° C.
Falling Film Reactor Cooling Temperature=90° C.
Feedstock Feed Rate=4.87 g/min The resulting acid (30 g, 34.3% activity) was neutralized with 1.5 g of 50 wt. % aqueous NaOH and 50 g of EGBE using standard mixing conditions at room temperature for 45 minutes and monitored over time for activity and pH as shown in Table 5.

TABLE 5

| pH[1] | % Actives[2] | Time (days) |
|---|---|---|
| 10.1 | 22.3 | 0 |
| 10.1 | 20.7 | 2 |
| 10.2 | 20.3 | 5 |
| 9.9 | 20.2 | 20 |

[1]pH measurements were made on a 1 wt. % aqueous solution of the neutralized product using a calibrated pH electrode.
[2]Determined via HYAMINE ® titration using 3864 for the sodium salt molecular weight.

The results summarized in Table 5 show that the use of EGBE as a co-solvent during the neutralization of the extra high molecular weight alcohol polyether alcohol provides efficient neutralization and good stability of the product.

As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

All documents cited in this application are herein incorporated by reference in their entirety to the extent such disclosure is not inconsistent with this text.

The invention claimed is:

1. A process for preparing an alcohol ether sulfate, the process comprising:
   (a) sulfating an alkoxylated alcohol having the structure

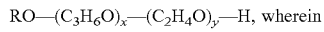
   $RO-(C_3H_6O)_x-(C_2H_4O)_y-H$, wherein

R is a $C_{12}$-$C_{40}$ aliphatic hydrocarbon group, x>1, y>1, and x+y≤100;
   (b) adding an aqueous base to the sulfated product of step (a) in the presence of a co-solvent having a flash point of at least 60° C., wherein the co-solvent is selected from polyhydric alcohols, alkylene glycol mono($C_1$-$C_6$ alkyl)ethers, polyalkylene glycols, polyalkylene glycol mono($C_1$-$C_6$ alkyl)ethers, or any combination thereof.

2. The process of claim 1, wherein the alcohol ether sulfate has a number average molecular weight of at least 2000.

3. The process of claim 1, wherein the alcohol ether sulfate is represented by the following structure:

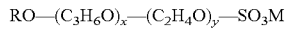
   $RO-(C_3H_6O)_x-(C_2H_4O)_y-SO_3M$ wherein:
   R is a $C_{12}$-$C_{40}$ aliphatic hydrocarbon group;
   x>1;
   y>1;
   x+y≤100; and
   M is an alkali metal cation, an alkaline earth metal cation, an ammonium cation or a substituted ammonium cation.

4. The process of claim 3, wherein R is a branched $C_{24}$-$C_{32}$ alkyl group.

5. The process of claim 3, wherein x is in a range from 20 to 50 and y is in a range from 5 to 15.

6. The process of claim 3, wherein x is in a range from 20 to 50 and y is in a range from 20 to 50.

7. The process of claim 1, wherein the sulfating step (a) comprises reacting the alkoxylated alcohol with sulfur trioxide, which has been diluted with air.

8. The process of claim 1, wherein the co-solvent has a flash point of from 60° C. to 300° C.

9. The process of claim 1, wherein the co-solvent has a flash point of from 65° C. to 250° C.

10. The process of claim 1, wherein the co-solvent is selected from the group consisting of ethylene glycol, propylene glycol, ethylene glycol n-butyl ether, diethylene glycol, triethylene glycol, tetraethylene glycol, dipropylene glycol, tripropylene glycol, diethylene glycol methyl ether, diethylene glycol ethyl ether, diethylene glycol n-butyl ether, triethylene glycol methyl ether, triethylene glycol ethyl ether, triethylene glycol n-butyl ether, polyethoxylated $C_2$-$C_4$ alcohols having from 5 to 25 ethylene oxide units per molecule, and combinations thereof.

11. The process of claim 1, wherein the weight ratio of the co-solvent to the sulfated product of step (a) is from 0.01:1 to 10:1.

12. The process of claim 1, wherein the base is an alkali metal hydroxide.

13. The process of claim 1, wherein the process is a continuous process.

* * * * *